| United States Patent [19] | [11] Patent Number: 4,950,469 |
|---|---|
| Katz | [45] Date of Patent: Aug. 21, 1990 |

[54] D-GL CONJUGATE THERAPY

[75] Inventor: David H. Katz, La Jolla, Calif.

[73] Assignee: La Jolla Pharmaceutical Company, San Diego, Calif.

[21] Appl. No.: 254,597

[22] Filed: Oct. 7, 1988

Related U.S. Application Data

[62] Division of Ser. No. 869,393, May 30, 1986, abandoned.

[51] Int. Cl.$^5$ .................... A61K 39/00; A61K 37/66; A61K 43/00
[52] U.S. Cl. .................... 424/85.1; 424/85.2; 424/85.8; 424/2; 424/9; 430/18; 430/21; 525/54.1
[58] Field of Search ............ 424/85, 86, 87, 88, 424/1.1, 2, 9, 85.1, 85.2; 525/54.1; 430/18, 21

[56] References Cited

U.S. PATENT DOCUMENTS

| 4,191,668 | 3/1980 | Katz | 424/91 |
|---|---|---|---|
| 4,545,985 | 10/1985 | Pastan et al. | 530/390 |
| 4,634,682 | 1/1987 | Erickson et al. | 530/300 |
| 4,861,581 | 8/1989 | Epstein et al. | 424/9 |
| 4,867,962 | 9/1989 | Abrams | 424/1.1 |

OTHER PUBLICATIONS

Katz, "Hapten-Specific Tolerance Induced by the DNP Derivative of D-Glutamic Acid and D-Lysine (D-GL) Copolymer", Immunological Tolerance, Academic Press, 1974.

Benacerraf et al, "Failure to Induce Tolerance to 2,4-Dinitrochlorobenzene Contact Sensitivity with a 2,4-Dinitrophenyl (DNP) Conjugate of a Copolymer of D-Glutamic Acid and D-Lysine, A Specific Tolerogen for DNP B Cells", The Journal of Immunology, vol. 112, No. 3, Mar. 1974, pp. 1158-1163.

*Primary Examiner*—Nathan M. Nutter
*Attorney, Agent, or Firm*—Irell & Manella

[57] ABSTRACT

Receptor blocking technology using proteins conjugated to polymers of D-glutamic acid and D-lysine for treatment of antibody-mediated autoimmune disease, membrane and tumor disorders is disclosed.

8 Claims, No Drawings

D-GL CONJUGATE THERAPY

This application is a division, of application Ser. No. 869,393, filed May 30, 1986 and now abandoned.

Background of the Invention

D-GL (D-glutamic acid:D-lysine copolymer) conjugates have been described at considerable length and various applications of D-GL conjugates of various immunologically reactive species have been reported. The following United States Patents describe in considerable detail the chemistry of D-GL and method of forming conjugates thereof: 4,191,668; 4,220,565; 4,222,907; 4,253,995; 4,253,995; 4,276,206; and 4,388,441. The technology underlying the invention is found in any of several treatises and reports of current advances, including, for example: METHODS IN ENZYMOLOGY, Academic Press, New York, e.g. in Volume 58, *Cell Culture* and Volume 68, *Recombinant DNA;* CELL BIOLOGY, Academic Press, New York (3 volumes); METHODS IN MOLECULAR BIOLOGY, Humana Press, Clifton, New Jersey; ADVANCES IN IMMUNOPHARMACOLOGY, Pergamon Press, New York; ADVANCES IN ALLERGOLOGY AND IMMUNOLOGY, Pergamon Press, New York, and in the current technical and patent literature.

The immunochemistry of D-GL conjugates is discussed and specific examples of immunochemical reaction, conjugation, and applications in diagnosis and treatment are discussed in the literature. See, for example, the above listed United States patents and the following publications. Katz, David H.; Davie, J. M.; Paul, W. E.; Benacerraf, Baruj *J. Exp. Med.* 1971 134(1):201–223; Nossal, J. V.; Davie, J. M.; Paul, W. E.; Katz, David H.; Benacerraf, Baruj *J. Exp. Med.* 1972 136(3):426–438; Katz, David H.; Toshiyuki, H.; Benacerraf, Baruj *J. Exp. Med.* 1972 136(6):1404–1429; Nossal, J. V.; Pike, B. L; Katz, David. H *J. Exp. Med.* 1973 138(1):312–317; Osborne, D. P.; Katz, David. H. *J. Exp. Med.* 1973 137(4):991–1007; Katz, David H.; Toshiyuki, H.; Benacerraf, Baruj *Proc. Nat. Acad. Sci. USA* 1973 70(10):2776–2780; Toshiyuki, H.; Katz, David H. *J. Exp. Med.* 1974 139:1446–1463; Katz, David H.; Toshiyuki, H.; Benacerraf, Baruj *J. Exp. Med.* 1974 139:1464–1471; Katz, David H.; Benacerraf, Baruj *Immunol. Tol.* 1974, 189–201 and 249–281; *J. Immunol.* 1974, 112(3):1158–1163; Ault, K. A.; Unanue, E. R.; Katz, David H. *Proc. Natl. Acad. Sci. U.S.A.* 1974, 71(8):3111–3114; Eshhar, Z.; Benacerraf, B; Katz, David. H. *J. Immunol.* 1975, 114(2):872–876; Katz, David H.; Stechsulte, D. J.; Benacerraf, Baruj *J. Allerg. Clin. Immunol.* 1975 55(6):403–410; Bullock, W. W., Katz, David H., Benacerraf, Baruj *J. Immunol.* 1975 115(1):272–277; Mosier, D. E., *Nature (London)* 1975:257:141-3; BitterSuermann, D.; Hadding, U.; Schorlemmer, H U.; Limbert, M.; Dierich, M.; Dukor, P. *J. Immunol.* 1975 115(2):425–30; Chiorazzi, N; Eshhar, Z; Katz, David H. *Proc. Natl. Acad. Sci. U.S.A.* 1976 73(6):2091–5; Katz, David. H.; Borel, Y. *J. Immunol.* 1978 120(6):1824–1827; Liu, Fu-Tong; Katz, David H. *Proc. Natl. Acad. Sci. USA* 1979 76(3):1430–1434; Liu, Fu-Tong; Bogowitz, C. A.; Bargatze, M. Z; Katz, Lee R.; Katz, David H. *J. Immunol.* 1979 123(6):2456–2465; Katz, David H. and Liu, Fu-Tong, ADVANCES IN ALLERGOLOGY AND IMMUNOLOGY, Ed. Oehling, A., Pergamon Press, New York (1980) pp. 51–59; Liu, Fu-Tong; Bargatze, R. F.; Katz, David H. *J. Allerg. Clin. Immunol.* 1980 66(4):322–326; Katz, David H. and Liu, Fu-Tong, ADVANCES IN IMMUNOPHARMACOLOGY, Ed. Hadden, J., Pergamon Press, New York (1980) pp. 277–284; Klinman, N. R.; Schrater, A. F.; Katz, David H. *J. Immunol.* 1981 126(5):1970–1973.

The published literature describes research into various immunochemical phenomena in an effort to understand the chain of immunological events and diagnostic methods and processes for detecting immunological species, e.g. antigens, haptens or antibodies to antigens or haptens.

The ability of D-GL conjugates to induce tolerance to a variety of antigens, haptens, nucleotides, nucleosides, etc. is described and, the ability of such conjugates to suppress antibody responses is mentioned, see, e.g., U.S. Pat. No. 4,191,668, David H. Katz, March 4, 1980.

The underlying premise in prior art methods and approaches is ability of selected D-GL-antigen conjugates to interfere with the induction of antibody responses and thereby modify, reduce or prevent the production of antibodies. In the process of studying antibody tolerance, it has been discovered that D-GL conjugates of cell surface receptor binding molecules which bind by specific receptors on the surface of cells and membranes stabilize such cell surface receptor binding molecules at the specific site and modifies, slows or prevents ingestion and/or migration of the receptor. This discovery has both therapeutic and diagnostic implications. For example, it is a feature of this invention to use cell surface binding molecule-D-GL conjugates to permit imaging of membranes, tumors, organs, etc. and to treat the surfaces of cells, membranes, tumors and organs by stabilizing cell surface receptor binding molecules which bind to receptor sites thereon. It is also a feature of this invention to treat membranes, tumors and the like by applying to the surface thereof cell surface binding molecule—D-GL conjugates to modify, slow or prevent the normal response of the cell surface receptor when coupled with a normal cell surface binding molecule.

SUMMARY OF THE INVENTION

The present invention encompasses the use of cell surface binding molecule—D-GL conjugates as direct therapeutic reagents in the treatment of cells, membranes, organs, tumors and the like.

The present invention also encompasses the use of cell surface binding molecule—D-GL conjugates as image enhancing reagents in the location, identification, and diagnosis of diseases or disorders of cells, membranes, organs, tumors and the like.

The invention may be described as a method of treating a disease or disorder of cells, membranes, tumors and the like which have surface cell receptors, and includes such steps as: identifying a cell surface receptor binding molecule having determinants which bind specifically to the cell surface receptors, forming a cell surface binding molecule—D-GL conjugate of the cell surface receptor binding molecule and introducing such D-GL conjugates into the patient.

The invention may also be described as a method of imaging cells, membranes, organ, tumors and the like which have surface cell receptors, and includes such steps as: identifying a cell surface receptor binding molecule having determinants which bind specifically to the cell receptors, forming a conjugate of the cell surface receptor binding molecule with D-GL, introducing such D-GL conjugate into the patient, associating an image forming moiety with the conjugate, and photographically, electronically or otherwise imaging the cell, membrane, organ, tumor or the like.

The invention contemplates cell receptor blocking reagents comprising D-GL conjugates of cell surface receptor binding molecules which bind specifically to cell surface receptors.

The invention includes methods and reagents for treating diseases and disorders of cells, membranes, organs, tumors and the like with cell surface binding molecule—D-GL conjugate which include toxins, pain suppressants, antibiotics, cell growth inhibitors, and other therapeutic reagents as moieties thereon.

The invention includes reagents comprising D-GL conjugates of proteins of the type produced by or in the course of an autoimmune response in a patient; e.g. synthetic duplicates of all or portions of such proteins, genetically engineered equivalents of such proteins, etc., or isolates of such proteins or portions thereof.

The invention also includes reagents comprising D-GL conjugates of proteins of the type produced by or in the course of a patient's response to activation by an antigen; e.g. synthetic duplicates of all or portions of such proteins, genetically engineered equivalents of such proteins, etc., or isolates of such proteins or portions thereof.

The invention contemplates the identification of a protein produced by a patient as a result of activation by an autoimmune response or to an xenogenous antigenic response and the injection of a D-GL conjugates of such proteins as a therapeutic method in treatment of the disease with which the response is associated.

DESCRIPTION OF THE PREFERRED EMBODIMENTS

The present invention comprises the introduction of selected conjugates of the copolymer of D-glutamic acid and D-lysine referred to generally as D-GL into the patient, animal or human, to interfere with or inhibit the progression of a disease or disorder and/or to define or diagnose the disease or disorder as to location, extent of invasion in the patient's body, type or characterization or otherwise to assist in the treatment and/or diagnosis of the patient's diseases or disorders.

In the discussion which follows, some terms are used in a more general sense than might be considered rigorous as a precise definition of the term. "Cell surface receptor binding molecule", for example, is used, unless otherwise indicated or modified, to mean a biological or biochemical species which acts as a single biological or physiological unit and which reacts with specific binding determinants upon the cells of a membrane, tumor, or other tissue. In many instances, such units are indeed single molecules. In other instances, such units may comprise more than one molecular entity, as the term molecular may be rigidly defined in the pure chemical bonding sense. Antibodies, generally, are single molecules and are within the meaning of the term "cell surface receptor binding molecule" as used herein. The essential feature of a cell surface receptor binding molecule as the term is used here, is that it is unitary in its physiological characteristics and binds selectively through specific determinants to cell surface receptors. The terms "reagent" and "moiety" are used in an interrelated sense, as follows, unless the context or modifiers indicate a different meaning. A "reagent" may be any chemical, biological or biochemical material which exhibits therapeutic or imaging characteristics and which can be reacted with, bound to, or associated with D-GL conjugates of this invention or to D-GL. A "moiety" may be any chemical, biological or biochemical adduct or substituent to D-GL conjugates of this invention or to D-GL as a precurser to such conjugates which exhibits therapeutic or imaging characteristics. "Therapy" and derivatives thereof as used here mean any function, phenomena, or treatment which is beneficial to the patient. "Patients" may be animals or humans. Receptor cell blocking means, as the term is used here, preventing reaction of the cell surface receptor in the way it would otherwise react when bound with a normal, unmodified cell surface receptor binding molecule; e.g., preventing or reducing the mobility of the receptor, preventing or reducing the ingestion of the receptor and/or the blocking cell surface receptor binding molecule, or modifying the normal physiological function of the cell surface receptor.

The following examples will illustrate the procedures, methods, compositions, and, to some extent, the mechanisms of this invention. The examples are intended to teach the concepts of the invention and are not limiting in any manner or degree as to the application, utility or scope of the invention.

The binding of a cell surface receptor binding molecule having determinants specific for a cell surface receptor may trigger one or more responses by the cell and in the host. Such responses may include migration of the receptor in the membrane, migration of the receptor into the cell where it may be metabolized to trigger an intracellular metabolic function, or to induce or suppress a group of cellular metabolic functions, transmission of a pain signal to the brain, proliferation of cells, synthesis of immunogen, histamine, complement factors, lymphokines, helper factors, suppressor factors or other physiologically active or activity inducing or suppressing substances. It has now been discovered that the presence of a cell surface binding cell surface receptor binding molecule-D-GL conjugate modifies such response. It is possible to block such responses in a negative manner, i.e. simply interfere with the normal response or the normal rate of response, or to modify the response in a positive way, i.e. induce a beneficial response, such as pain reduction or prevention, promoting healing, etc. By including an imaging moiety, the cell surface, tumor, etc. may be imaged for diagnostic purposes. All such reactions are referred to here as "blocking" because all involve blocking the cell receptor from binding with a cell surface binding cell surface receptor binding molecule which would induce the normal response.

T-cells are characterized by the presence of cell surface receptors which are capable of specifically binding antigens, though the exact nature of these receptors is not fully understood. There is some evidence that the T-cell surface receptor consists of one or two chains, but this has not been established to the complete satisfaction of all immunologists. The presence of cell surface binding molecules, antigens, on T-cells is manifest in the response of the T-cell vis-a-vis a particular activation of the T-cell. It is generally recognized that there is an interdependence between the antigen and MHC (major histocompatibility complex), but universal agreement upon the nature and extent of this interdependence has not been reached. It is sufficient for present purposes to recognize that it is difficult and in most instances impossible to predict what, if any, change in response may be expected from the reaction of T-cell surface receptors with changed cell surface binding molecules. There is substantial agreement that lectin- and antigen- activated T-cells produce the lymphokine referred to as T-Cell Growth Factor (TCGF) and interleukin-2 (IL-2). TCGF is a protein (MW 12,000–17,000) whose activity allows the long-term proliferation of T-Cells followed by interaction with antigen. TCGF has been implicated in the maintenance of T cell malignancies (Gootenberg, J. E., et al *J. Exp. Med.* 1981 154:1403). Natural killer cell activity may also be stimulated by TCGF (Henney, C. S. et al, *Nature* 1981 291:335). TCGF exists naturally in only very small amounts; however, recent advances in recombinant DNA technology have made it possible to obtain TCGF in amounts suitable for rather detailed studies and other laboratory purposes. According to this invention, D-GL conjugates of TCGF, TCGF-D-GL conjugates are introduced, by injection for example, into the patient where such TCGF-D-GL conjugates will specifically bind to and inhibit the proliferation of TCGF dependent tumor cells, such as leukemias and lymphomas. It is significant that the specific cell surface binding molecule—D-GL conjugate, TCGF-D-GL, without any other reagent moiety has therapeutic effect. Further, if a specific tumor expresses TCGF receptors, the TCGF-D-GL conjugate will bind to these receptors, thus offering diagnostic applications and by interfering with non-conjugated TCGF binding to the tumor expressed TCGF receptors differentiating between tumor and non-tumor express TCGF receptors, differentially inhibiting proliferation of tumor cells and be of therapeutic value. Tumor toxic moieties attached to the D-GL backbone bound via the TCGF-D-GL conjugates act directly upon the tumor and may reduce or prevent the proliferation of tumor cells and may kill existing tumor cells, depending upon the specific tumor toxic moiety utilized.

TCGF expressing hybridoma have been described (Tanaguchi, et al. *Nature* 1983 302:305) and the sequence thereof reported TCGF is coupled to D-GL by the methods described by Katz (U.S. Pat. Nos. 4,191,668 and 4,276,206). The resulting conjugate is suspended in a physiologically acceptable solution, e.g. isotonic saline solution, and injected periodically, e.g. daily, in amounts of from a few nanograms to 100 micrograms the most efficacious amount being determined by starting with a minimum injection and increasing the injection while observing the tumor growth pattern until the growth is arrested and/or reversed Injections may be into the blood stream or peritoneal fluid or introduced adjacent to the tumor to be treated, or into a body fluid stream which enters an organ with which the tumor is associated.

Myasthenia gravis is an autoimmune disease in which the patient forms autoantibodies against muscle-cell receptors which normally recognize and bind acetylcholine—the neurotransmitter released from nerve endings. Muscle movement signals are blocked and muscular weakness results In addition to antibodies against acetylcholine receptors, autoantibodies against striated muscle fibers and thymic tissue, and, on occasion, other autoantibodies may be produced by the patient. If it were possible to selective block the binding of the autoantibodies to acetylcholine receptors, muscle movement signals could reach these receptors, thus interrupting the chain of muscle weakening and other debilitating effects of myasthenia gravis. Conjugates of D-GL and acetylcholine receptor, the gene for which has been cloned and is becoming well defined, prepared by the method of Katz, supra, in a suitable physiologically acceptable carrier solution injected in amounts of from less than a nanogram to over 100 micrograms per day, on a periodic basis such as daily, will suppress the autoimmune response of the body to acetylcholine receptor antibody, thus reducing the progress of myasthenia gravis. In some instances, where diagnosis is early, this treatment may reverse the progress of the disease and allow the muscles to rebuild lost strength by regular use.

Rheumatic fever is also believed to involve an autoimmune response to streptococcal antigens that are expressed by other tissues, especially cardiac tissue. The disease causes inflammation of joints and cardiac tissue, for which there is presently no specific therapy. D-GL conjugates of antigens which specifically bind anti-Strep A antibodies, if injected in the microgram or submicrogram range, may be expected to interfere with the autoimmune response which is believed to be implicated in rheumatic fever. As specific autoantigens are idenified and isolated, D-GL conjugates thereof may also interfere with the inflammation response and halt or diminish the rate of progress of the disease. Such D-GL conjugates may include inflammation reducing moieties, antibiotics and other therapeutic moieties coupled through D-GL and the antigen to bind to the membrane surface, thus concentrating the therapeutic agent on the membrane surface.

Distinct cell surface cell surface receptor binding molecules are associated with various tumors, and are expressed differentially at high concentrations on the surface of some tumors. D-GL conjugates of anti-tumor antibody will bind specifically to the tumor, interfering with normal tumor growth. Therapeutic agents, e.g. radioactive atoms or toxins, which could not be tolerated on a whole-body basis may be coupled through D-GL to the specifically binding antibody, thus directing the therapeutic agent to the tumor, concentrating the radiation, toxicity or other therapeutic effect on the tumor surface where the therapeutic effect is maximized and the overall side reaction is minimized Beta and soft gamma emitting radioisotopes which normally have little or no value in therapy may be used with great effect because they are on the surface of the tissue to be attacked. Since the D-GL conjugate will concentrate preferentially on the tumor surface and will otherwise be spread throughout the body, the whole-body radiation is minimal while effective levels of radiation are concentrated on the tumor surface.

$I^{-131}$ labeled cell surface binding molecule—D-GL conjugate may be used, for example, in the treatment of tumors which respond to radiotherapy by forming a conjugate of $I^{-131}$ labeled D-GL with the cell surface binding molecule which binds specifically to the tumor. The radiation of the $I^{-131}$ decay acts directly and immediately upon the tumor with minimal radiation upon other organs. A number of procedures for labelling reagents with $I^{-131}$ and other radiolabels are disclosed in *HANDBOOK OF RADIOIMMUNOASSAY, Guy E. Abraham,* Marcell Dekker, Inc., New York, 1977, the references cited therein and in the more recent literature. Other radiolabels may, of course, be used to accomplish desired types, levels and lengths of radiation therapy to a particular tumor.

In some instances, through only minor invasion of the body, the cell surface binding molecule D-GL-therapeutic conjugate may be applied directly to or adjacent the tumor, thus permitting the direct and most efficient binding of the therapeutic agent specifically to the tumor with minimum migration through the body. This procedure may be carried out, for example, by using X-ray viewing or other techniques to guide the tip of a hypodermic syringe to the desired location and introducing the cell surface binding molecule D-GL conjugate on or adjacent the tumor. Injection may, as in the above examples, be through the blood circulatory system.

In addition to the purely therapeutic applications referred to, the size, shape and location of a tumor may be determined with considerable accuracy using the technique described to attach a visualizing moiety such as a radioactive or radiopaque to the backbone of the D-GL of the cell surface binding molecule—D-GL conjugate or to the molecule thereof, and directing the conjugate to the tumor.

Industrial Application

The present invention has general application to therapy in diseases in which receptor blocking technology is involved, and to the use of use of proteins conjugated to polymers of D-glutamic acid and D-lysine for treatment of antibody-mediated autoimmune disease.

What is claimed is:

1. A method of inhibiting the proliferation of T-Cell Growth Factor-dependent tumor cells in a patient comprising introducing an effective amount of D-GL T-Cell Growth Factor conjugate into the patient.

2. A method of treating a patient for a lymphokine-dependent malignancy which comprises administering to the patient an effective amount of a D-GL lymphokine conjugate.

3. A method of selectively killing tumor cells in a patient which comprises administering to the patient an effective amount of a radiolabeled cell surface binding molecule D-GL conjugate wherein the cell surface binding molecule is specific to the tumor cells and the radiolabel is cytotoxic to the tumor cells.

4. A method of imaging tumor cells in a patient which comprises administering to the patient a radiolabeled cell surface binding molecule D-GL conjugate wherein the cell surface binding molecule is specific to the tumor cells and visualizing via the radioactivity emitted by the radiolabel the tumor cells in the patient to which the conjugate binds.

5. A method of selectively killing tumor cells in a patient which comprises administering an effective amount of D-GL cell surface binding molecule-cytotoxic agent conjugate to the patient wherein the cell surface binding molecule is specific to the tumor cells.

6. The method of claim 5 wherein the cell surface binding molecule is an antibody.

7. A method of imaging specific cells in a patient comprising administering to the patient a D-GL cell surface binding molecule-visualizing moiety conjugate, wherein the cell surface binding molecule is specific to said cells, and visualizing the cells to which the conjugate binds.

8. The method of claim 7 wherein the cell surface binding molecule is an antibody.

* * * * *